United States Patent [19]

Lang

[11] 4,083,957
[45] Apr. 11, 1978

[54] PROCESS FOR THE ALTERATION OF THE SEX-RATIO OF MAMMALS

[76] Inventor: John L. Lang, P.O. Box 1242, Midland, Mich. 48640

[21] Appl. No.: 655,237

[22] Filed: Feb. 4, 1976

Related U.S. Application Data

[63] Continuation-in-part of Ser. No. 491,881, Jul. 26, 1974, abandoned, which is a continuation-in-part of Ser. No. 272,343, Jul. 17, 1972, abandoned, Ser. No. 224,225, Feb. 17, 1972, abandoned, and Ser. No. 874,405, Nov. 5, 1969, abandoned, each is a continuation of Ser. No. 653,670, Jul. 17, 1967, abandoned, which is a continuation-in-part of Ser. No. 222,638, Sep. 7, 1962, abandoned.

[51] Int. Cl.² ............................................. A61K 31/74
[52] U.S. Cl. ....................................... 424/78; 424/79; 424/80; 424/81; 424/82; 424/83; 424/105
[58] Field of Search ..................... 424/78, 81, 105, 79, 424/80, 82, 83

[56] References Cited

PUBLICATIONS

Chemical Abstracts, vol. 81, (1974), p. 45990m.
Chemical Abstracts, vol. 81, (1974), p. 88994h.

*Primary Examiner*—V. D. Turner

[57] ABSTRACT

The invention provides an improved method for alteration of the sex ratio in animal (including human) offspring by separation of the population of spermatozoa into fractions which are different by reason of the sex-linked electrical charge resident thereon. The separation is carried out by bringing the spermatozoa into close association with an electrostatic charge-bearing material having a charge the sign of which is opposite to the sign of a chosen portion of the spermatozoa which carries the sex determining character of the unwanted sex, so as to attract and thereby to permit that portion to be isolated, or put to a disadvantage in the fertilization of ova. The invention is concerned with the selection of the charge-bearing material, the adjustment of the pH and particle size thereof, and the control of the surrounding medium in relation to its influence on the charge characteristics of both the charge-bearing material and the spermatozoa.

20 Claims, No Drawings

PROCESS FOR THE ALTERATION OF THE SEX-RATIO OF MAMMALS

REFERENCES TO RELATED APPLICATIONS

This application is a Continuation-In-Part of now-pending but herewith abandoned application Ser. No. 491,881 filed July 26, 1974 for "PROCESS FOR THE ALTERATION OF THE SEX-RATIO OF MAMMALS", which herewith abandoned application is a Continuation-In-Part of abandoned application Ser. Nos. 272,343 filed July 17, 1972; 224,225 filed Feb. 17, 1972; and 874,405 filed Nov. 5, 1969 respectively for "PREDESTINATION OF SEX", which Applications were in turn Continuations of a still earlier Application, also now abandoned, Ser. No. 653,670, filed July 17, 1967 for "PREDESTINATION OF SEX"; which yet earlier application was a Continuation-In-Part of also abandoned application Ser. No. 222,638 filed Sept. 7, 1962 for "PREDESTINATION OF SEX".

BACKGROUND OF THE INVENTION

It is known that there are, for all practical purposes, equal numbers of male and female determining spermatozoa at the locus of parental fertilization in the reproductive process in the vast majority of higher animals, including humans. The effect of this is that in general a nearly equal ratio of male and female decendants results from the reproductive processes of the population of the entire species.

This naturally-occurring ratio is disadvantageous in many instances and for certain purposes. For example, in the dairy industry, the female is generally desired for the production of milk, but in some cases a male is highly desired from a particularly good female. In the beef industry, the premium is on males.

In the rabbit industry, females are in demand because the female rabbit only is employed in the Ascheim-Zondeik Murray pregnancy test.

It has been known for some time that living spermatozoa can be concentrated to some extent according to their sex-determining character by electrophoresis. Thus, the migration of living sperm cells under the influence of a direct current electrical field can be observed by microscopic examination.

The electrophoretic method has been described by a number of workers in this field, e.g., V. N. Schroeder, Biol. Shur. 1. 24–29, (1932); 3, 465–476, (1934); 5, 657–689, 690–722, (1936); 6, 1235–1250, (1937); Bull. Acad. Sci. U.R.S.S., Ser. Biol., pp. 426–455, (1940); Compt. Rend. Acad. Sci. U.R.S.S. 26, 692–697 (1940); Z. Tierzuckt Zuchtungsbiol. 50, 1–15 and 16–23; (1941); Uspekhi Sovremennoi Biol. (Moscow) 28, 211–225, (1949); A. A. Siljander, Sbornik Trudov Zootek. Kaf. s.h. Skol. Kirov., pp. 148–166, (1936); and M. J. Gordon, Proc. Nat. Acad. Sci., 43, 913–918, (1957).

In the electrophoretic process the charged spermatozoa are attracted to an appropriately charged electrode. One of the problems with electrophoresis is that, when sufficient voltage is used to produce an adequately strong separating force, electrolysis also occurs. This causes an insulating hydrogen barrier to appear on the surface of the electrode which interfers with the operation of the process. Thus, relatively low voltages are required for the electrophoretic method, and the separating forces are relatively weak. Also, with the electrophoretic method, the spermatozoa are required to move comparatively long distances between the electrodes before separation or even concentration can be achieved. Thus, the weakness of the forces involved and the length of the distances required, render the electrophoretic method seriously slow. This is a major disadvantage because the life span of the spermatozoa is relatively short. The result is that the hitherto known electrophoretic methods only show a very modest degree of separation for treating times of sufficiently short duration to be practical. In fact, the entire operability of the electrophoretic method has been seriously challenged, (Hafs, H. D. and Boyd, L. J.; Am. Soc. Anm. Sci. Symposium Minutes 7/31/70 to 8/1/70, pp. 85–97).

It is also known that the spermatozoa of the respective sexes have different sizes and weights, the female portion being larger and heavier. In addition, possibly due to its smaller size and weight, the male can move more rapidly. However, the nearly equal ratio of male and female offspring occurring in nature would indicate that, despite the increased motility of the male bearing spermatozoa, approximately equal numbers of males and females arrive simultaneously at the locus of parental fertilization. The differences between the sizes and weights of the spermatozoa of opposite sexes are due to differences in the amount of genetic material, that is, between the X-chromosome (female) and the Y-chromosome (male). From the available weight data, it is known that there is a probability of about 87.5% that a randomly chosen female-determining spermatozoa will be heavier than a randomly chosen male-determining spermatozoa. The actual weight and size differences, however, are not great. Thus, the difference between the extremes in weight which is reported in the literature is only about 6.2%. The size difference is comparable. Such differences are not sufficient to permit good separation of the respective sex-determining portions by simple filtration, sedimentation or centrifugation within periods of short enough duration to be practical.

Notwithstanding the disadvantages of the known methods for separating spermatozoa according to their sex-linked characteristics, the results have at times shown promise. For example, according to the publication of Gordon, Supra, using a known electrophoretic technique, out of 167 births in 31 litters of rabbits, the desired sex of the offsring was obtained 113 times. Thus, the involved success ratio was about 67.7%. However, the loss of spermatozoa was so great as to render the process of doubtful practical value. On the other hand, after conducting a much more extensive test by the electrophoretic method, Hafs was unable to demonstrate any degree of pre-selection, thus creating serious doubt as to the validity of the entire electrophoretic concept. The other known processes which rely on the size, weight, or motility differences of the spermatozoa have likewise shown only mild promise.

Accordingly, prior to the present invention, despite the demand for a process by which the sex of mammals could be safely and efficiently pre-selected, no known process has achieved the goal in a sufficiently certain or efficient manner to be considered practical.

SUMMARY OF THE INVENTION

My invention builds from the fact that the spermatozoa having respectively male or female sex bearing genetic material, (herein referred to as "male" and "female" spermatozoa), also have differing electrostatic charges. There is considerable debate in the field as to whether there is an charge at all, whether it is different for the respective sexes, and which sex carries which charge if the charge exists. However, my observations demonstrate strongly that there is a charge, that it differs between the males and the females, and that it is normally negative for the male and positive for the female in the spermatozoa of all the mammals I have been able to observe (bovine, rabbit, human, hamster).

My observations include, first, the observation of spermatozoa under the influence of an electrostatic field as in electrophoresis. The spermatozoa definitely migrate at least to some degree and leave at least a partially rarified area half-way between the electrodes. When the insulating, hydrogen barrier builds up on the positive electrode, the observed migration ceases, but at least the initial migration demonstrates electrostatic selectivity. I attribute the virtual failure of the electrophoretic method not to any fault in its theoretical basis, but to its inherent mechanical problems such as the hydrogen barrier, and the distances involved. In addition, since the spermatozoa of the respective sexes are charged so as to attract each other electrostatically, the applied electrostatic field in the electrophoretic method must at least be strong enough to overcome the attraction, and even if separation is effected temporarily reconstitution of the balance between the sexes will proceed much more rapidly than the separation. These factors impede the electrophoretic method.

Other observations confirm the existance of a charge of opposite sign on the spermatozoa of the respective sexes. Thus, dye-staining of human spermatozoa with quinacrine produces a yellow spot on the "F-body" of the male spermatozoa. The curious part about this is that the Y (male) chromosome itself does not stain with quinacrine because both quinacrine and the Y chromosome are positively charged, whereas the negatively charged X (female) chromosome does stain with quinacrine. This indicates that an electrostatic reversal of sign takes place between the inside of the spermatozoa and the surface of the cell membrane. I am not certain why this takes place, but it points to the existence of complex relationships between the proteinaceous substance of the cell membrane and its surrounding medium which control the nature of the charge. On the other hand, the fact that there is a selective dye staining between the respective sexes supports a conclusion that there are different charge characteristics between the sexes.

Another and even more convincing proof that the respective spermatozoan groups are differently charged follows from the fact that when they are dispersed in a colloidal suspension of an ion exchange resin having a given charge and a particle size of, for example, one-half the size of a spermatozoa, about one-half of the spermatozoa are seen to be literally attached to discrete particles and the other half are swimming free. The attached ones are not dead. They appear to be struggling to get free, but yet they are greatly hampered in their motility. Further observations (quinacrine dying with human spermatozoa and field tests on animal spermatozoa) show that the free ones belong predominantly to one sex or the other depending upon the effective signs of the charged particles and the spermatozoa in the particular medium. As far as I am aware, I am the first to have observed this, and it is my discovery of this which forms the basis of this invention.

Accordingly, the basic and primary step in the practice of my invention is to bring the spermatozoa into close association with a charge-bearing material so as to create an electrostatic bond between the material and the fraction of the spermatozoan population which has a sex characteristic opposite to the one desired for breeding. Having once established the bond further separating steps are taken.

The close physical positioning between the spermatozoa and the charge bearing material, and the subsequent separation are obtained by various techniques. A typical way is to prepare a filter bed or column of beads of the charge-bearing material, and to pass the spermatozoa through it in a liquid medium. This effects both contact and separation rapidly. Anotherway is to mix the spermatozoa with a suspension or solution of the chargebearing material, and thereafter to separate the particles out by sedimentation, centrifugation or electrophoresis, or by permitting the more motile group to separate itself from the bound group by their own action. The process can be carried out in some circumstances by a douche associated with natural copulation, in which case the spermatozoa of the undesired sex are not removed but merely immobilized.

In any of the alternatives for obtaining physical closeness between the charge-bearing material and the spermatozoa with my process it will be seen that the desired closeness of contact takes place rapidly. Also subsequent release of the bound spermatozoa by treating the charge-bearing material with a charge-releasing agent is possible. For instance, spermatozoa bound to a positively-charged ion exchange resin can be washed free with an isotonic 2.9% sodium citrate solution; spermatozoa bound to a negatively charged resin can be washed free with an isotonic solution of tris (hydromethyl) amino methane hydrochloride. When promptly carried out, this provides a further fraction of spermatozoa of sex-determining ratio different from that of naturally occurring spermatozoa.

The basic requirement for the charge-bearing material is simply that it must provide a multiplicity of points where the appropriate charge exists when the material is immersed in the treating medium. Thus, the surface must provide charged sites predominantly of a given sign, and, since the flow of electricity is not involved (and not desired), the charged sites are separated by non-conducting material. A wide variety of materials can be used depending upon the nature of the liquid medium. In general, any of the natural or synthetic polyelectrolytes can be used. For example, the various ionizable forms of polymers which contain monomers such as alpha, beta unsaturated carboxylic acids including acrylic acid, maleic acid, itaconic acid, vinyl benzene sulfonic acid, polyelectrolyte reaction products of vinyl benzyl chloride or vinyl benzyl bromide with nucleophilic reagents, including trimethyl amine, to give vinyl benzyl trimethylammoniom chloride, vinyl pyridine, vinyl pyrrole, vinly pyrrolidone, vinyl oxazolidinone, other polyamines, vinyl benzene sulfonic acid, carboxylated polymers, sulfonated polymers, phosphonic acid polymers, including the various forms thereof, such as natural and synthetic ion exchange resins, modified cellulosics, charged natural and synthetic colloidal dispersions such as the positively or negatively charged silver bromide sols prepared as described in "Experiments in Colloid Chemistry" by E. A. Hauser and J. E. Lynn, page 74, McGraw-Hill Book Company, New York, 1940, natural and synthetic lattices, colloid charged by electrosorption, many chargeable proteinaceous materials, (e.g. egg white) some of the materials ordinarily thought of as unionized or non-ionic, as polyacrylamide, but which have charge sites, the porous zeolites popularly called molecular sieves, which can be further loaded to confer enhanced or altered charge sites, also clay minerals per se or so loaded which materials are herein referred to as polyelectrostatic charge-bearing materials.

While any of the foregoing materials and their equivalents may be used, further consideration must also be given to the constituents of the liquid medium in which the treatment is to be carried out and their effects on both the charge-bearing material and the surface of the spermatozoa. In the process, a sample of seminal fluid is obtained by conventional procedures. It is then mixed with a diluent and brought into contact with the charge bearing material which is also immersed in the diluent. The diluent, of course, must be substantially isotonic, and its temperature and its pH as well as its other constituents, must be suitable for maintaining live spermatozoa. Various suitable formulae for such diluents exist, but not all are compatible with my process. Thus certain substances which are employed to control the osmotic pressure of the diluent and its pH, may have an interferring effect on the charge relationship between the spermatozoa and the charge-bearing material. The constituents of the diluent therefore must be selected according to standard chemical procedures in order to avoid the use of ions which have bond strengths which do so interfere with the separation of the two species of spermatozoa.

Another factor of major importance is the accuracy of pH control. It will be understood that the pH of the diluent has an influence on the charge relationship between the spermatozoa and the charge-bearing material. Also it is important to use the optimum pH so as to create the maximum contrast between the charge of the spermatozoa to be immobilized and the charge of the charge-bearing material. The reason why pH is important is that the proteinaceous cell membrane of the spermatozoa is amphoteric and its charge reverses in sign depending upon pH. Thus, with all the spermatozoa I have observed, the best immobilization of females comes on the acid side around pH 5.8 to 6.2 and the best male immobilization at approximately pH 7 to 7.5. Separation occurs with varying degrees of success outside of these ranges but when a substantially lower or higher pH is employed either the entire population is immobilized or it is totally unaffected, and hence no selective separation occurs. Accordingly, an accurate control of the pH is important to my process.

Two aspects of pH control must be considered. First, some of the charge-bearing materials which can be used in my process are also amphoteric. This simply has to be taken into consideration with respect to the pH of the diluent and the isoelectric point of those materials as well as that of the spermatozoa. With these factors in mind, the process is then controlled in such a way as to provide maximum contrast (consistent with a healthy environment for the spermatozoa) between the charge of the spermatozoa which one wishes to immobilize and the charge-bearing material. Of course, a proteinaceous material which has the same isoelectric point as the spermatozoa which one desires to immobilize, will not be effective to immobilize that spermatozoa because its charge will always be the same as that of that spermatozoa regardless of the pH.

The second aspect of pH control has to be with migration of ions within the charge-bearing material. Typical commercially available ion-exchange resins generally have a major predominance of acidic or basic ions. The diluent passing through a filter-bed or column employing such resins may have its pH adjusted to a desired apparent value but yet, an extremely thin layer may exist at the surface of such a resin, which layer has a vastly different pH than the surrounding solution due to the ions migrating to the surface. Also time is a factor. Initially the pH can drift rapidly after adjustment. In a typical case I have found that it can take as much as 10 weeks of continous pH adjustment to reach a point where observable migration ceases. On the other hand, some of the materials which are suitable for my process exhibit very little migration. For instance, Bentonite clay is negatively charged, and although its charge is relatively weak, it exhibits virtually no migration dependent upon pH. The point, however, is either to thoroughly equilibrate, or to select materials which need no equilibration.

Another thing to avoid is the use of constituents in the diluent which will coat or otherwise have a masking effect on the charge-bearing material. For instance, egg yolk is often employed as a constituent in diluents for seminal fluids. However, when an ion exchange resin is employed, as the charge-bearing material in my process, one must avoid the use of egg yolk in the diluent because it coats the resin and interfers with the process. Of course after separation has been achieved, the egg yolk can then be added without problem.

In general, recognizing that the objective is to establish an electrostatic bond between spermatozoa of one charge and a charge-bearing material having the opposite charge, the operator must simply follow sound chemical procedures taking into account the nature of all the materials he is using and the possibility of interfering interaction therebetween.

In the general order of their importance, the factors affecting the spermatozoa separation efficiency are:

1. The nature of the treating agent, as, e.g., the physical size thereof and the molecular architecture such as branching, linearity, the cross-linkage degree therein, and the nature of the electrical charge;
2. The pH relationships of the treating agent vis-a-vis the spermatozoa;
3. The heighth of the percolation bed, when this particular method of the invention is used;
4. The nature and pH of the diluent or carrier fluid;
5. The species of animal spermatozoa being treated, which affects a) the pH of the individual ejaculate, and b) the amount of extraneous material in the ejaculate;
6. The velocity gradient of any fluid flow at the treating agent - spermatozoa loci;
7. The disparity of the sign of the electrical charge on the various parts of the treating apparatus;
8. The conditions of time and temperature of the treating system, as to their effect on spermatozoan lifespan.

Since the spermatozoa are largely composed of amphoteric substances, e.g., proteins, etc., the treatment can be successfully carried out over wide ranges of pH, especially when accompanied by compensating changes in the diluent system. This acid-alkaline relationship is susceptible to understanding in its similarity to the behavior of other amphoteric materials other than spermatozoa. The pH alteration, of course, must be such that spermatozoa life is not jeopardized severely or quantitatively.

In summary, my invention therefore broadly comprises bringing spermatozoa into close association with a material the composition of which provides a multiplicity of electrostatically charged sites predominantly of one electrostatic sign, in an isotonic liquid medium pH, temperature and other constituencies of which are controlled to maintain the live spermatozoa in an electrostatically charged state in which the spermatozoa of one sex have a charge opposite to that of the other sex in substantially the same ratio as is forund in nature, and to maintain said material in a state in which, together with the ions in the solution provide a predominance of charged sites on the material of one sign only whereby a predominant portion of the spermatozoan population of one sex becomes attached to the charge-bearing material, followed by separating (or identifying) the so attached spermatozoa from the free ones by reason of their attachment to the charge-bearing material.

Features of prime importance are the rapid exposure of the spermatozoa to a large surface-to-volume ratio of the charge-bearing material and consequent rapid segregation or identification, the use of a charge-bearing material which carries its own charge and which therefore becomes attached in situ without reliance on applied forces for attachment, and the use of conditions which do not decrease the vitality of the spermatozoa. Once attachment has been formed, separation of the spermatozoan groups can be achieved by numerous techniques including mechanical action such as filtering in which the charge-bearing material is fixed to a base and the free spermatozoa simply are carried off in the effluent, sedimentation, centrifugation, electrophoresis, magnetism (by incorporating magnetic substances in the resin or polyelectrolyte), or by the greater inertia of the charge-bearing material whereby the more motile, unbound spermatozoa separate themselves from the bound ones by their own action.

EXAMPLES

General

The separation of the spermatozoa according to the process of the invention, is always carried out under such conditions adapted for preservation of the vitality thereof. Thus a substantially isotonic solution is used. While considerable latitude exists in temperature conditions, rapid changes in temperature are apt to be harmful. Also particular care must be taken to maintain an almost normal osmotic pressure. The range of permissible osmotic-pressure values is well known in the art, and much data exists pertaining to suitable "diluters" or "extenders" for spermatozoa. The most widely known of these is "normal saline", or approximately 0.87% sodium chloride solution in water. Solutions of 0.78–0.9% or 0.154 molar sodium chloride are commonly sufficiently similar that their use is permissible. Others include "Krebs-Ringer" buffer, "Krebs-Henseleit-Ringer" buffer, phosphate citrate buffer (0.05–0.15 molar); sodium citrate in about 2.9 weight percent concentration, "Tris" (an almost isotonic solution of tris (hydroxymethyl) amino methane and citric acid in water; skim milk, and the like; the solution is prepared to have about the same osmotic properties as the fluids found in the animal concerned, and should have relatively non-interfering character in terms of its interaction with either the spermatozoa or the treating agent.

Also, when the spermatozoa are to be stored in a frozen state, it is generally required to use special "extenders", which may include chicken egg yolk or derivations thereof, glycerol and other substances to prevent excessive "freeze-kill" of the spermatozoa. In cases where such constituents will coat the charge-bearing material, they are added after separation is achieved.

In the following Examples, "Krebs-Henseleit-Ringer Buffer" (herein K-H-R buffer) refers to the following composition:
  100 ml of 0.9 wt % aqueous NaCl
  4 ml of 1.15 wt % aqueous kcl
  1 ml of 2.11 wt % aqueous KH2PO4
  1 ml of 3.82 wt % aqueous MgSO4.7H2O
  2 ml of 1.30 wt % aqueous NaHCO3
  0.5 g fructose
  0.1 g normal gelatin "Krebs-Ringer" (herein K-R) refers to a composition of:
  100 ml 0.154 molar sodium chloride
  4 ml 0.154 molar potassium chloride
  with the pH adjusted with appropriate additions of 0.12 molar $KH_2PO_4$ and 0.12 molar $Na_2HPO_4$.

The invention is further illustrated and demonstrated in and by the following exemplary illustrations.

EXAMPLE I

A 0.4 weight percent solution of poly(vinylbenzyltrimethylammonium chloride) was prepared with the KHR buffer solution. Natural bull seminal fluid containing live spermatozoa was diluted in a 1:1 ratio by volume with the KHR buffer solution. A drop thereof was then placed on each of two microscope slide cover glasses. To one of these was added the above solution in an amount which adhered to ¼ inch of the lip of a dissecting needle. Cover glasses were emplaced over the cavities of a dual cavity culture-type microscope slide and examined at magnifications of 600× and 900×.

The treated sample contained both unaffected, live mobile spermatozoa, and flocculated (i.e. handicapped, immobilized or inhibited) or attached spermatozoa in about equal proportion.

In the control sample, only mobile live sperm cells could be observed. None appeared to be handicapped.

In a complementary experiment flocculation of one portion of the spermatozoan population by a positively charged polycation was carried out. The supernatant fluid in the treated sample was drawn off and microscopic examination at 600× showed that part of the sperm population was indeed live, mobile and free (but and of course) diminished in number. The control sample exhibited no change from the original. In the flocculated portion, spermatozoa could be seen associated with the polycation.

Similar and equivalent results were obtained by the use of various positively-charged ion exchange resin powders, polyvinylpyridine, quarternized polyvinylpyridine, other poly-electrolyte reaction products of vinylidene benzyl chloride or vinylidene benzyl bromide with nucleophilic reagents, vinyl pyrolle, vinyl pyrollidone, vinyl oxazolidinone, polyethylenimine, poly-electrolyte reaction products of nucleophilic reagents with chloro-methylated or bromomethylated poly (vinylidene aromatic compounds) positively-charged colloidal particles, positively-charged silver chloride sols, and positively-charged clays and other minerals. Such materials come within the definition of "poly-electrostatic charge-bearing materials" as herein used.

Likewise, a flocculation was carried out using whole bull semen with poly (vinylbenzyltrimethylammonium chloride) wherein separation of spermatozoan populations by the method of the invention at a pH of about 7.28 at a concentration of 1000 ppm was carried out.

These examples demonstrate separation by a mechanism which appears to be electrostatic attraction. They do not demonstrate, per se, that the separation is between the respective sexes, and I do not cite them for that purpose, but merely to establish the identity of a mechanism of spermatozoan separation by the use of many similar polyelectrolytes.

EXAMPLE II

A 0.5 weight percent solution in "K-H-R buffer" of a sulfonated polystyrene prepared according to the methods outlined by H. H. Roth, in Ind. Eng. Chem., 49, 1820 et seq., (1957) was adjusted to about pH 7.1 by addition of sodium hydroxide was used to treat seminal fluid, diluted 1:2 with KHR buffer, as described in the above Example I, in one cavity of a dual cavity culture-type microscope slide. The other cavity contained untreated seminal fluid, at the same concentration.

The mixing of the treated sample produced a partial clumping or aggregation of the sperm which was visible to the unaided eye. Examination at 400× under a microscope revealed the presence of both mobile, individual and clustered or aggregated handicapped spermatozoa.

In a further test, there was added to 2 milliliters of the 1:2 diluted seminal fluid about 1 drop of the above-described solution of sulfonated polystyrene salt. In 15 minutes, partial clustering of spermatozoa resulted in formation of precipitate. Microscopic examination of the supernatant liquid showed many unflocculated, mobile living sperm cells.

In a similar experiment, a sulfonated polystyrene ion exchange resin was ground to a fine powder, and used as the treating agent for sperm in one cavity of a dual cavity culture-type microscope slide. Examination at 600× and 900× showed that in the treated portion, the surface of the ion-exchange resin particles were partly covered with adherent sperm cells, in addition to which there were about an equal number of unattached mobile, live sperm cells. Sperm cells could be seen to approach the resin particles, and be repelled and in some cases move away. In other cases, they would not be repelled, but would adhere thereto. In the untreated portion, only individual, mobile sperm could be seen. Another observation of a similar sample disclosed the presence of spermatozoa which had fine particles of the ionexchange resin stuck to the head, the tail, or both. These sperm could only move with difficulty. Again separation by electrostatic attraction appears to be the mechanism of the separation.

In similar experiments, charged proteinaceous materials such as raw chicken egg white mutually diluted with isotonic sodium chloride was used at pH values of 5.0, 7.2 and 8.0; these experiments likewise exhibited the effect of partially and selective handicapping of spermatozoa. The proteinaceous material was observed to selectively become attached to a portion of the spermatozoa, handicapping the mobility of the thus-attached spermatozoa, while the unattached spermatozoa were freely mobile in the fluid media.

Similarly, poly(maleic anhdride), prepared according to the method described in the Journal of Polymer Science, Vol. 55, Issue 162, pages S-31, S-32, (1961), in 0.5 weight percent solution in K-H-R diluent with the pH adjusted to 7.1 with sodium hydroxide by producing flocculation of the positively-charged portion of the spermatozoa population of semen treated therewith, leaving the negatively-charged sperm free to move to and fertilize ova, as was observed at 100× and 600× under a microscope.

Also, poly(acrylic acid), poly(methacrylic acid), itaconic acid polymers, poly(vinylbenzene sulfonic acid), poly (vinyl sulfonic acid), carboxymethyl cellulose silicic acid gels, negatively-charged "white water" from papermaking, negatively-charged latex particles, negatively-charged silver bromide sols, and a powder form of a phenol sulfonic acid formaldehyde condensation resin, when buffered to the proper pH values, were used to treat sperm cells, with similar and equivalent results. Such materials come within the definition of "poly-electrostatic charge-bearing materials" as herein used.

Examination of sperm treated with linear weakly acidic polymer (sodium:polyacrylate); the rather lightly cross-linked weaklyacidic copolymer (known as "ASE 60" from Rohm & Haas Co., Philadelphia, Pa.); the rather tightly cross-linked weakly acidic ion-exchange copolymer (known as "Rexyn 102" from Fisher Scientific Co. of Pittsburgh, Pa., Catalogue No. R184); a linear and rather lightly cross-linked and strongly acidic ion-exchange sulfonated styrene divinylbenzene copolymer (known as "Dowex 50" from the Dow Chemical Company of Midland, Michigan and having the properties listed in Table A, page 44 and 44a); the linear weakly basic poly(ethylene imine); another rather tightly cross-linked weakly basic ion-exchange resin (known as "Rexyn 206" from Fisher Scientific Co.); the rather lightly (i.e. easily swellable in water) cross-linked strongly basic quaternized emulsion copolymer of vinyl benzyl chloride; and cross-linked copolymers of methacrylic acid and a difunctional monomer, such as divinyl benzene, trivinyl benzene, glycol dimethacrylate, etc. (prepared preferably, for example, by a reverse suspension polymerization technique with 0.03% divinyl benzene); and the rather tightly cross-linked strongly basic (quaternized chloromethylated copolymer of 92 weight % styrene and 8 weight % divinylbenzene) materials, shows that the specificity of the treatment of the invention may be altered and/or enhanced by, amongst other factors, alteration of the degree of cross-linking of the macromolecular polyelectrolyte treating agents of the invention.

This, coupled with the tendency of positively-charged spermatozoa (females in most species) to precipitate negatively-charged linear polyelectrolytes in the correct experiment, and vice-versae, indicates the desirability for using cross-linked or "insoluble" electrostatically-charged treating agents.

Notably, increasing the cross-linking also expands the range of allowable concentration before physical entrapment becomes a factor.

This is not to say that soluble materials do not work, but that there are advantages in employing the insoluble form.

This cross-linkage to which I refer, is the normal form of "insoluble" materials, such as minerals, charged colloidal materials, and so forth; the action by these latter are affected by variation of the particle size thereof, pH adjustment, and/or the ionization range of the functional group providing the electrostatically charged site of the treating agents according to the rules of physical and colloidal chemistry.

The foregoing examples still do not demonstrate, per se, which sex is segregated by which charge, or even that the segregation is along the lines of sex, but merely that a remarkably similar appearing segregation takes place when the electrostatic charge environment is controlled to create one charge relationship or the other between the charge-bearing material and the spermatozoa. The following examples deal with the proof of segregation along lines of the respective sexes.

EXAMPLE III

One of my earliest tests dealt with an attempt to alternate the sex-ratio of rabbit offspring.

Rabbits produce offspring in litters and, according to Cole and Cupps in "*Reproduction in Domestic Animals*", in rabbits the number of ova produced is always greater than the number of individuals in the litter. Since each member of a litter is a result of a separate fertilization of an ovum by a sperm cell, each individual litter member has the same chance of being either a male or a female on the same basis as is the case where animals are born in single births, such as cattle, sheep, horses and the like.

Rabbit semen was collected from a buck rabbit using a technique equivalent to that reported by C. Mac Irons and A. Walgon, J. Agri. Sci., 28, 122, (1938). The semen was diluted with isotonic diluent (K-H-R buffer diluent), and mixed with an electrostatically charged treating agent at an adjusted pH value (see Table I), and stored in a refrigerator until used.

The female rabbit was prepared either by allowing a vasectomized male rabbit to stimulate her for several hours before she was to be inseminated, or with pituitary luteinating hormone. She was either anesthetized with 1.2 milliliters of a 10% solution of sodium iso-amyl ethyl barbiturate, immobilized during the artificial insemination.

After the gestation period, the sex of the young were determined by the microbiological method, also used by Gordon, as reported in Proceedings of the National Academy of Science, Vol. 43, pp. 914–917, (1957), by sectioning, staining and microscopic examination of the gonads or by raising the young until the sex could be determined visually.

Table I

| Treating Agent | No. Females | Treating Conditions | pH | Males | Females |
|---|---|---|---|---|---|
| Control | 2 | Natural copulation | — | 7 | 9 |
| Sulfonated polystyrene sodium form (negative) | 3 | 200 ppm | 7.02 | 3 | 18 |
| Quaternary amine polymer chloride form (positive) | 2 | 1000 ppm | 7.02 | 10 | 3 |

This example showed a sharp cleavage along sexual lines. The insemination was performed by taking a portion of the sample from the bottom of a tube and, evidently, the flocculated and settled portion of the sample was inseminated into the rabbit rather than the supernatant. In addition, the fluids in the vaginal cavity evidently released the bound spermatozoa so as to permit conception. I was not specifically aware of this at the time of this early test, but my later tests have confirmed this conclusion.

EXAMPLE IV

Another series of experiments employed a soluble poly (acrylic acid) equilibrated in an isotonic solution for treating rabbit spermatozoa before insemination. The polyacrylic is weakly acidic and negatively charged when ionized.

Conversely, a weakly basic positively charged, polyethylene imine derivative, likewise equilibrated in isotonic solution, was used in a complementary test.

In these tests the negatively charged polyacrylate immobilized the positively charged females, and using the supernatant portion of the sample more males were born. Conversely, the positively charged imine attracted the negatively charged males and more females were born.

Table II

| Treating Agent | Concentration ppm | pH | Males | Females | Success Ratio (%) |
|---|---|---|---|---|---|
| Polyacrylate | 200 | 6.5 | 19 | 12 | 61.3 |
| " | 400 | 6.8 | 8 | 6 | 75.0 |
| " | 800 | 6.8 | 21 | 8 | 72.4 |
| " | 600 | 7.5 | 89 | 61 | 59.4 |
| Polyimine | 200 | 7.5 | 5 | 8 | 61.5 |

EXAMPLE V

In another experiment, semen collected from eight male rabbits was pooled and divided into three parts. One-third thereof was diluted with K-H-R buffer solution at a pH of 7.2 using, for the adjustment, a 1.54 Molar aq. $KH_2PO_4$ plus sodium reagent additions in a titration-like procedure until the desired pH was obtained. This was the semen used in the control.

The charge-bearing material employed "Polyimine Treating Agent — 1". It composed 0.1 ml of a 0.6 wt. % solution of poly [oxyethylene (dimethyl imino) ethylene (methylimino) - ethylene dichloride], a positively charged material obtained commercially as Polymer No. 7971 from the Tim Hennigan Engineering Division of W. D. Mann Company of Hinghan, Mass. (U.S.A.), diluted with 1.87 ml of K-H-R buffer at a pH of 8.3.

One-third of the raw semen was treated with "Polyimine Treating Agent — 1" at a pH of 6.5 using a ratio of about 1 ml of the semen to 2.0 ml.

The remaining third of the semen was diluted with a solution designated as "SPA-1". It comprises a negatively-charged polyelectrolyte solution at the ratio of 1 ml of raw semen to 0.1 ml at 2000 ppm concentration in K-H-R buffer of poly(acrylic acid: sodium salt) (Polymer No. 7930 from the above-identified Hennigan Engineering Division) at pH 7.5; to which was then added 1.65 ml of K-H-R buffer at pH 6.0.

Doe rabbits which had been isolated for 16 days to eliminate "pseudo-pregnancy" effects were stimulated by injection into the circulatory system of 2.5 milligrams of standard pituitary luteinating hormone to induce ovulation. Then, each of the does was inseminated with 0.2 ml of the appropriately treated rabbit semen. They were checked for pregnancy at 18 days by palpation of the abdomen.

After 29 days gestation, the does were killed and the feti taken surgically, to prevent possible cannibalism of all or part of a naturally-born litter.

The gonads of the feti were removed, then embedded, sectioned and stained so that the sex of each fetus could be determined by microscopic examination.

The following data were obtained which demonstrates that the supernatant portion of the spermatozoa contains spermatozoa having differing sex-ratio character than the settled portion thereof:

The control does and the does that were inseminated immediately after the preparation step of the semen treatment produced litters in which the sex of the offspring exhibited a wide scatter between male and female, as given and reproduced in the following tabulation:

Table III

| Treatment | Males | Females |
|---|---|---|
| Control Doe No. 1 | 3 | 3 |
| Control Doe No. 2 | 1 | 0 |
| "Polyimine Treating Agent 1" as mixed and unsettled | 4 | 5 |
| "SPA-1 Treating Agent" as mixed and unsettled | 3 | 5 |

Four does were inseminated with spermatozoa that had been separately treated with "Polyimine Treating Agent 1" and five does inseminated with "SPA-1 Treating Agent", allowed to settle, and the supernatant portion removed carefully for insemination.

The results obtained are given in the following tabulation:

| Treatment | Males | Females |
|---|---|---|
| "Polyimine-1" at pH 6.5, then 8.3 | 5 | 8 |
| "SPA-1" at pH 7.5, then 6.0 | 16 | 7 |

These ratios of sexual reproduction results are 0.384 and 2.28 respectively, as contrasted with the natural 1:1 ratio.

Here the positively charged "Polyimine-1" attracted the male spermatozoa resulting in more female births, and conversely the negatively charged "SPA-1" attracted the female spermatozoa and caused more male births.

That the settled portion of the treated spermatozoa contains a population whose sex-determining ratio is different than that in the supernatant is shown by the following table, which also shows that spermatozoa bound to this treating agent can be liberated therefrom by the substances in the reproductive tract of the female rabbit:

Table IV

| | F | M | Ratio F/M |
|---|---|---|---|
| Inseminated After Mixing with "SPA-1" at pH 6.8 | 6 | 7 | 0.86 |
| Settled about 20 Minutes | 14 | 7 | 2.00 |
| | F | M | Ratio F/M |
| Inseminated After Mixing with "SPA-1" at pH 7.5 | 7 | 11 | 0.64 |
| Settled 20 Minutes | 13 | 11 | 1.18 |

EXAMPLE VI

Tests were run on various dairy cattle, including Jerseys, Holsteins and Guernseys, wherein the seminal fluid of the bull was treated with sodium polyacrylate (which polymer had a net charge that was negative) at various pH values and concentrations. In general, the seminal fluid which was used in a volumetric amount of about 2.4 ml total by dilution to a concentration of about 30 million sperm per ml with adequate quantities of aqueous sodium citrate of about 2.8 weight %, 20 weight % egg yolk and 7 weight % glycerol, all at an initial pH of about 7.4.

No control sample was run in these tests, but something similar thereto was done. Thus, in one series we employed the settled or flocculated portion only (see Examples 1-5). In another series we inseminated the seminal fluid immediately after mixing (see Examples 6-12, Table V below). In a third series (Examples 13-16) we employed only the supernatant.

Table V

| Cow No. | Treatment* | Fetal Age (In Days) At Examination | Sex |
|---|---|---|---|
| 1 | A (1) | 93 | Female |
| 2 | A (1) | 91 | Female |
| 3 | A (1) | 92 | Female |
| 4 | A (1) | 89 | Female |
| 5 | A (1) | 91 | Female |
| 6 | A (2) | 76 | Male |
| 7 | A (2) | 76 | Male |
| 8 | A (2) | 75 | Female |
| 9 | A (2) | 75 | Female |
| 10 | A (2) | 75 | Female |
| 11 | A (2) | 75 | Male |
| 12 | A (2) | 80 | Female |
| 13 | B | 78 | Male |
| 14 | B | 76 | Male |
| 15 | B | 76 | Male |
| 16 | B | 86 | Male |
| 17 | C | 84 | Female |
| 18 | C | 83 | Female |
| 19 | D | 79 | Female |

*A - Sodium Polyacrylate at 500 ppm, with pH of treating solution 6.3 and final seminal pH 6.9.
B - Sodium Polyacrylate at 500 ppm, with pH of treating solution 7.2 and final seminal pH 7.28.
C - Sodium Polyacrylate at 25.0 ppm, with pH of treating solution 6.0 and final seminal pH 7.0.
D - Sodium Polyacrylate at 12.5 ppm, with pH of treating solution 6.0 and final seminal pH 7.0.
(1) Indicates that seminal fluid after treatment was permitted to stand for 5-10 minutes to settle.
(2) Indicates that seminal fluid was used immediately after treatment.

In these tests cows 1-5 demonstrate the effect of the negatively charged resin in attracting and segregating the female spermatozoa from the remainder of the population. They also demonstrate that at least with a polyacrylate, the environment of the cow's vaginal tract effectively liberates the bound female spermatozoa. Cows 6-12 represent virtually a null result as one would expect from insemination of both bound and free spermatozoa under circumstances in which the bound ones will become liberated in the vaginal tract. Cows 13-16 represent carrying out the process at a pH of 7.28, and employing only the supernatant. This resulted in four successive male births. The remaining three cows cannot be regarded as a sufficient number to be significant for any given test. In fact, the mere five cows of Series A(1) and the mere four cows of Series B, cast some doubt on the validity of basing conclusions on those tests alone.

EXAMPLE VII

In another test cattle semen was treated with polyacrylate (negatively charged) at a total concentration of about 50 ppm and a pH of about 7.4. A diluent mixture comprised of about 2.8 weight % of sodium citrate; 20% chicken egg yolk; and 7% glycerol was used. The supernatant was then put in ampules having about an 0.8 ml capacity at a concentration of about 30 million motile sperm per milliliter. The charged ampules were sealed, frozen in liquid nitrogen and then stored according to the conventional procedure.

Cows is oestrous (i.e., "in heat") were inseminated artificially using commonly employed and accepted professional procedures for the purpose. After gestation periods of from 60 to 70 days, the fetal calves were taken by laparotomy and the sex of each then determined. Fourteen calves were obtained using the bull semen treated as above described.

The results obtained were:

With Treated Semen     10 Males     4 Females

This test added to Series B of the previous test provides a more convincing statistical proof of my conclusion. Additional tests on cows are described later in this specification.

EXAMPLE VIII

A separate series employing quinacrine dye techniques on human spermatozoa was performed.

The quinacrine dihydrochloride or quinacrine mustard staining techniques for identification of the Y chromosome in human semem is disclosed and explained, inter alia, in the following references: Zechs, Exp. Cell. Res. 58, 463, (1969); P. L. Pearson, M. Bobrow, & C. G. Vosa, Nature, 226, 78–80, (Apr. 4, 1970); P. L. Pearson, & M. Bobrow, Nature, 226, 959–961, (June, 1970); P. Barlow & C. G. Vosa, Nature 226, 961–962, (June 1970); Editorial Anonymous Nature, 226, 897 (June 6, 1970). This technique provides an excellent guide for determination of the sex ratio of the spermatozoan population from which the effectiveness of given treating agents may be evaluated. It also provides a basis for correlating the effects of treating agents on the semen of animals, the spermatozoa of which are not identifiable by quinacrine staining.

This procedure involves examination of spermatozoan using ultraviolet fluorescence microscopy at suitable magnification, (e.g. 970X) to detect the so-called "F-body". [the "F-body", as is known, has been proven definitive for presence of the Y-chromosomes which are comparable to karyotype (i.e., the counting or typing the genes or chromosomes in the cell) for purposes of tissue comparison.]

In normal semen from normal males of the more general XY-type, half of the spermatozoa show the presence of only a single F-body on each, while the other half has no indication of F-bodies whatever therein or thereon.

The quinacrine dye-staining method became definitive for Y-chromosome detection when it was found that about one-half of spermatozoa of the so-called XYY "supermale" individuals exhibited two such "F-bodies".

This experiment concerns the use of this accepted analytical tool in evaluation of the spermatozoa separation process of the application.

Human seminal fluid was allowed to "liquify" (i.e., de-gel by enzymatic action) for 30 minutes at 37° C, and diluted in a 1:3 proportion with a Krebs-Ringer buffer at a pH of about 7.2. A column of negatively charged 16–50 mesh sulfonated copolymer of styrene with between 4 to 12 weight percent therein of copolymerized divinyl benzene ("Dowex 50W") (sodium form) and a height of the column of about 500 mm, was equilibrated with the same buffer at the same pH and checked immediately before use. Eight ml of the above-described diluted semen was introduced at the top of the column. It was then percolated through the column, with the effluent exiting the column at the rate of about 1 drop per second.

Cuts of the effluent, in volumes of about 1 ml each, were made and prepared as slides by further dilution and spread on a freshly-cleaned non-fluorescing slide, and allowed to dry thereon.

The slides were then "set" by immersion in absolute alcohol for five (5) minutes, and stained in a 1 weight % quinacrine dihydrochloride composition for about twenty (20) minutes; then washed in distilled water at least three times each by thorough rinses until no yellow color was discernable to the eye on the slide sample. Each of the slides was then covered with a water-wet 24×40 mm slide cover, and the edges of each of these sample specimens was then sealed with a clear lacquer.

Observation in the ultraviolet fluorescence region with Y48 barrier filters, infra-red absorbing and ultraviolet transmitting illumination at 350 nanometers (i.e., "nm") using a "Swift" brand ultraviolet fluorescence microscope at 1000X clearly showed by easily evident discernment the "F-body" in approximately one-half of the blank sperm sample which had been diluted in about 1:25 ratio with distilled water.

Examination of the prepared slides from the column effluent cuts (or fractions) by scanning each one thereof under ultraviolet fluoresence illumination at 350 nm using a microscopic scanning technique of at least one entire right-to-left path across each specimen slide showed a remarkably altered ratio between the sperm with- and without- the "F-body", as the data in Table VI below illustrates:

Table VI

| Cut (or Fraction) No. | F-Body Observed | No F-body Observed |
|---|---|---|
| 1 | Very few Spermatozoa Present | Very Few Spermatozoa Present |
| 2 | " | " |
| 3 | " | " |
| 4 | 4 | 62 |
| 5 | 21 | 162 |
| 6 | 8 | 208 |
| 7 | 8 | 320 |
| 8 | 16 | 352 |
| 9 | 3 | 64 |
| 10 | 7 | 111 |
| 11 | 2 | 145 |
| 12 | 2 | 103 |
| 13 | 13 | 213 |
| 14 | 7 | 111 |
| 15 | 8 | 107 |

After treatment, in Cuts No. 4–15, inclusively, the ratio of "No F-body"/"F-Body" was 2121:85 for the 2,206 sperm cells that were randomly observed; with a ratio of about 26:1 as compared to the virtually 1:1 ratio observed in the blank samples or the 1.8:1 ratio reported by Barlow and Vosa, supra. Since the "F-Body" has been shown conclusively to be a feature of the male-determining human spermatozoa, the chances of a female descendant resulting from fertilization using the treated live sperm would be about 20 to 26 times greater when an ovulating female is so-inseminated with the treated spermatozoa than when fertilization is accomplished by the use of untreated or an average naturally-occurring sperm sample or product.

Microscopic examination of particles of ion exchange material taken from the top of the column showed that spermatozoa cells were attached to the surface thereof.

This test, however, introduced a curious problem. Although it showed a sharp cleavage along sexual lines, the negatively charged resin attracted the negatively charged male spermatozoa. I believe this was due to the presence of the strongly reactive positive sodium ions in the environment and migrating from the surface of the resin. This apparently changes the charge relationship between the resin and the spermatozoa such that the female spermatozoa are repelled from the resin and the males are attracted. I am not certain of this explanation, but I have more recent data which confirms it.

EXAMPLE IX

In another experiment, human spermatozoa-containing fluid was passed through a bed of negatively charged "Dowex 50W" (sodium form) in a 3/16 inch diameter column that had a height of 150 mm and which had been equilibrated with 0.8% NaCl and 0.154 Molar sodium phosphate at a pH of about 7.15.

Examination of three samples prepared from the effluent containing the treated semen after staining with quinacrine dihydrochloride showed respectively ratios of "F-Bodies"/"No F-Bodies" of 2:34, 3:32, and 1:32, corresponding respectively to the male-to-female ratios in the treated spermatozoa.

Similarly, percolation through 700 mm of 16–50 mesh sized "Dowe×50W", (sodium form) equilibrated with about 0.1 Molar sodium phosphate-sodium citrate at a pH of about 7.18, followed by slide preparation and staining as above, showed ratios of "F-Body"/"No F-Body" of 1:18, 17:208, and 2:242 respectively.

Again, the negatively charged resin did not attract the positively charged female spermatozoa under ionic conditions similar to Example VIII and presumably for the same reasons.

EXAMPLE X

Tests on human spermatozoa which confirm my explanation of Examples VIII and IX, were conducted using a phosphate-citrate buffer (0.5m) as follows with the following results:

Table VII

| Resin Type | pH | F-Body Ratio Treated / Normal |
|---|---|---|
| Carboxylic acid resin (sodium form) (negative) "Biorex-70" (weakly acid) | 6.0 | 1.45 |
| " | 6.0 | 1.34 |
| " | 6.0 | 1.77 |
| " | 6.0 | 1.36 |
| " | 6.0 | 1.30 |
| " | 7.2 | .84 |
| " | 8.0 | .69 |
| Sulfonic resin (hydrogen form) "Dowex 50W-X8" (negative) (strongly acid) | 6.0 | 1.25 |
| " | 6.0 | 1.24 |
| " | 7.2 | 1.45 |
| Sulfonic resin (sodium form) "AG50W-X8" (negative) (strongly acid) | 6.0 | 0.66 |
| " | 6.5 | 0.43 |
| " | 7.2 | 0.74 |
| " | 7.2 | 0.47 |
| " | 7.2 | 0.59 |
| Phosphonic acid resin (sodium form) "Biorex 63" (negative) (intermediate acid) | 6.0 | 1.14 |
| " | 7.2 | 0.57 |
| " | 8.0 | 1.31 |
| Quaternary Amine resin (chloride form) "AG1-X8" (positive) (strongly basic) | 6.0 | 0.42 |
| " | 7.2 | 0.79 |
| " | 8.0 | 0.56 |
| Quatenary-Tertiary Amine - Mixed (chloride form) | 6.0 | 0.80 |
| "Biorex 5" (positive) Intermediate Base | | |
| " | 7.2 | 0.11 |
| " | 8.0 | 0.95 |
| Alkylene Amine-Mixed (Chloride form) "AG3-X4A" (positive) Weak Base | 6.0 | 0.18 |
| " | 6.0 | 0.63 |
| " | 6.0 | 0.64 |
| " | 7.2 | 0.52 |
| " | 8.0 | 1.19 |

(Trademarks in the above Table refer to products of Bio Rad Laboratories, Rockville Center, New York, and the Dow Chemical Company of Midland, Michigan.)

The above table shows that with the carboxylic resin at a pH of 6.0 the positively charged female spermatozoa were attracted to the negatively charged resin whereas a pH of 7.2 and 8.0 the opposite occurred. Since the only change was to increase the concentration of the highly reactive sodium ions (positive) with a corresponding decrease in proportion of hydrogen ions, since, with the carboxylic acid resin form, such a change is sufficient to bring the sodium ions into a position of dominance in the ionic relationship of the components, and since the only effect of such a change (of which I am aware) is to change the effective charge relationship of the components, it follows that the change in sex of the attracted spermatozoa was due to the change in the effective electrostatic charge relationship.

The other resins follow similar and consistent patterns. Thus, the negatively charged sulphonic resin (hydrogen form) "Dowe x-50W" attracts the female spermatozoa even at pH of 7.2 because it has a surface on which the hydrogen ions predominate, at least until a complete equilibration at that pH has been effected, at which point it can no longer actually be regarded as being "in the hydrogen form".

In the sodium form, the negatively charged sulphonic acid resin "AG50-W-X8" attracts the negative males and repels the positively charged female spermatozoa not only at a pH of 7.2 according to the previous examples, but also even at an apparent pH of 6.0 and 6.5. I say "apparent" because in this test, an incompletely equilibrated resin was used, and sodium ions were still predominant at its surface even though the general environment was mildly acidic.

The negatively charged phosphonic acid (sodium form) "Biorex 63" exhibited an even more complex reaction. At pH of 6.0 it mildly attracted the female spermatozoa. At pH 7.2 it showed a relatively strong tendency to repel the female spermatozoa, whereas at pH 8.0 it again attracted the females. This apparent inconsistency is due, in my opinion, to the association of the phosphate ion of the resin with the citrate ion of the buffer which produces an ionized carboxylic acid resin having a negative charge in proportion to the amount of citrate associated with it.

The final three amine resins follow the same pattern. They are positively charged bases and therefore one would expect them to attract the males at both low and high pH, and they do. The sole exception is with the weakest base "AG3-X4A", which at pH of 8 is actually not ionized. One would expect a null from it at that pH. The test showed a slight predominance of males passing through the column, i.e. 1.19, or virtually a "null" reading.

EXAMPLE XI

A field test on cattle was conducted using the following method of the invention:

Tubes or columns of polycarbonate plastic 1.25 meters long were fitted with a filter pack of polypropylene fiber with a nominal height of 25 mm immediately above a stop-cock. The column diameter was 25 mm. The columns were filled to a height of 900 mm with a slurry of ion exchange resin having either a positive or a negative electrostatic charge. The ion exchange resin was one which had been equilibrated to a selected pH value for at least sixteen hours.

In this test, the positively-charged resin had an aminofunctional (electrical charge site) group; (Dowex 1, chloride form, having the properties listed in Table A, page 44 and 44a); the negatively-charged sulfonic acid functional (electrical-charge site) group (Dowex 50W, having the properties listed in Table A, page 44 and 44a). Dowex 50 is prepared by co-polymerizing styrene with divinylbenzene, and subsequently sulfonating it with concentrated sulphuric acid, a reaction which proceeds quantitatively throughout the resin grains, introducing one sulphonic acid into each benzene ring. The structure of the resulting resin is:

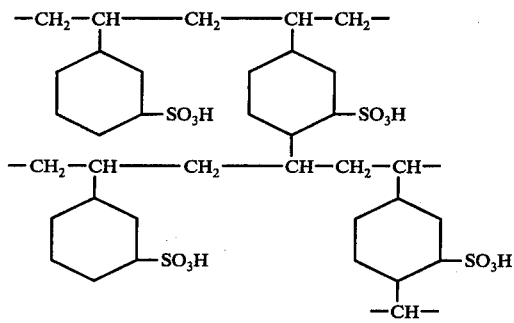

Furthermore, the proportion of cross-linking rings is directly controlled by the proportion of divinylbenzene to styrene used in the reaction mixture. Dowex 50W has the same chemical properties as Dowex 50, and differs only with respect to physical properties, such as its greater exchange stability and its white coloring.

The diluent carrier for the bull semen was a conventional one, viz. "Tris diluent", which is an isotonic solution of the salt of tris (hydroxymethyl)-amino-methane with citric acid in doubly-distilled sterile water. The pH of this diluent was adjusted to the selected value (see Table VIII) by addition of the proper ratio of two solutions; one was a 0.12 molar disodium hydrogen phosphate in doubly-distilled sterile water, and the other was a 0.12 molar solution of mono-potassium di-hydrogen phosphate in doubly-distilled sterile water.

Shortly before introduction of the bull spermatozoa into the column, a sufficient amount of the diluent was perculated through the column to assure that the column was both at the correct pH value and that the spermatozoa would be in a hospitable environment for their survival.

The bull semen was collected in the conventional manner, cooled in a water-jacketed container to 16° C over a period of one-half hour, and introduced into the top of the treating column, all operations being conducted in a room maintained at 16° C. The spermatozoa-containing effluent was collected, and centrifuged in 15 ml centrifuge tubes, using an Arthus H. Thomas Co. "Super Roto" centrifuge, the centrifuging conditions varied from ten minutes at 800 r.p.m. to 20 minutes at 2500 r.p.m., depending upon the resin type used and the pH selected. The correct conditions were selected by visual observation at intervals. The usual amount of spermatozoa-containing effluent was 200–250 ml, the centrifugation was carried out in a cold room maintained at 10° C.

The supernatant fluid from the centrifuged spermatozoa-containing effluent was removed by means of a Pasteur pipette, and the thus-concentrated spermatozoa combined and the volume measured. The number of spermatozoa per milliliter was counted, and diluted to a value of eighty (80) million per milliliter with "Tris"-diluent to which was added sufficient chicken egg yolk to total twenty (20) percent egg yolk in the total volume, and then re-diluted to a spermatoza concentration of forty (40) million per milliliter by slowly adding it to an extender which contained the "Tris" diluent, twenty (20) percent egg yolk, and fourteen (14) percent glycerol.

This "extended" treated bull semen was sealed in the conventional containers used by cattle artificial inseminators, then cooled and frozen in liquid nitrogen for storage, these operations being carried out by the conventional procedures of the art.

Cows in oestrous were inseminated with the bull semen treated by this method of the invention, the inseminations were carried out by ordinary cattle inseminators, using conventional techniques. The "non-return" ratio, i.e., the percentage of cows which became pregnant as a result of only one insemination, was approximately the same as that "non-return" ratio obtained when using semen which had not been treated by this variation of the process of the invention. In the overall test, the "non-return" ratio for the bull semen treated by this variation of the invention was 68.2% the "non-return" ratio for the conventionally extended, untreated semen from the same bulls was 69.9%.

The 1284 calves born as a result of this test were normal in every observable respect.

Table VIII

| Expt. No. | Nominal Electrical Charge of the Treating Agent | pH | Total Calves | Success Ratio |
|---|---|---|---|---|
| 1 | Positive | 7.3 | 353 | 1.49F: 1.00M |
| 2 | Positive | 7.8 | 229 | 1.46M: 1.00F |
| 3 | Negative | 7.5 | 454 | 1.43F: 1.00M |
| 4 | Negative | 6.3 | 248 | 1.47M: 1.00F |

Of these tests, No. 1 is consistent with Table VII (AG1-X8), and No. 4 is consistent with Table VII "Dowex 50X-X8". Nos. 2 and 3 are not consistent with Table VII, but there was an important difference between the tests of Table VII and VIII, in the diluents employed. In the tests on Table VIII the diluent was a Tris-citrate (see above), whereas in the tests on Table VII it was a sodium phosphate-sodium citrate. In addition, the pH adjustment for the tests of Table VIII was made by adding the Tris ion as distinguished from adding the sodium ion as in the tests of Table VII. Thus, in test No. 2 of Table VIII, the Tris had to be increased in order to raise the pH to 7.8. This excess of positively charged Tris apparently neutralized the negative male spermatozoa permitting them to pass through the column, and conversely, the excess of negatively charged citrate ions effectively dominated the resin causing it to attract the positively charged female spermatozoa. In test No. 3 of Table VIII an opposite effect occurred. In that test when the excess of Tris was present at pH 7.5 the positively charged Tris associated itself with the negatively charged resin, and the negatively charged citrate effectively neutralized the positive female spermatozoa. This allowed the females to pass through the column and permitting the resin to behave as though it were positive and thereby to attract and negatively charged male spermatozoa.

TABLE A

Properties For Standard Cross-Linked Ion Exchange Resins

|  | DOWEX 1 | DOWEX 50 | DOWEX 50W |
|---|---|---|---|
| TYPE | Strongly Basic Anion Exchanger | Strongly Acidic Cation Exchanger | Strongly Acidic Cation Exchanger |
| Active Group | Trimethyl Benzyl Ammonium | Nuclear Sulfonic Acid | Nuclear Sulfonic Acid |
| Standard Crosslinkage (% Divinylbenzene by Weight) | 8 | 8 | 8 |
| Special Crosslinkages (% Divinylbenzene by Weight) | 1,2,3,4,8,10,16 | 1,2,4,5,8,10,12,16 | 1,2,4,5,8,10,12,16 |
| Matrix | polystyrene | Polystyrene | Polystyrene |
| Effective pH Range | 0–14 | 0–14 | 0–14 |
| Selectivity | $Cl^{31}/OH^-$=approx. 1.5 | $Na^{30}/H^+$=approx. 1.2 | $Na^{30}/H^+$=approx. 1.2 |
| TYPE |  |  |  |
| Order of Selectivity | $I>NO_3>Br>Cl>$ Acetate$>OH>F$ | Monovalent $Ag>Cs>Rb>K>NH_4>NA>H>Li$ Divalent $Ba>Sr>Ca>Mg>Be$ | Monovalent $Ag>Cs>Rb>K>NH_4>Na>H>Li$ Divalent $Ba>Sr>Ca>Mg>Be$ |
| Total Exchange Capacity (Wet) Meq. gm | ($Cl^-$ form) 1.4 | ($Na^+$ form) ($H^+$ form) 1.9    1.7 | ($Na^+$ form) ($H^+$ form) 2.0    1.8 |
| Total Exchange Capacity (dry) meq/gm | ($Cl^-$ form) 3.5 | ($Na^+$ form) ($H^+$ form) 4.8    5.0 | ($Na^+$ form) ($H^+$ form) 4.4    4.8 |
| Maximum Thermal Stability (° C) | ($OH^-$ Form), ($Cl^-$ form) 50   ,   150 | 150 | 150 |
| Physical Form | Spheres | Spheres | Spheres |
| Standard Mesh Range | 20–50 (Wet) | 20–50 (Wet) | 20–50 (Wet) |
| Ionic Form as Shipped | $Cl^-$ | $H^{30}$ or $Na^+$ | $H^+$ or $Na^+$ |
| Shipping Density (lb/cu ft) | 44 | ($Na^+$ form) ($H^+$ form) 53    50 | ($Na^+$ form) ($H^+$ form) 53    50 |
| Moisture Content (%$H_2O$) | 43–48 | — | 44–48    51–54 |

EXAMPLE XII

A further experiment was conducted specifically in order to take into account the known variation in the sex-ratio of offspring calves from one bull to another, and also the known day-to-day variation in sex-ratio of calves produced by individual bulls. In this test, each bull ejaculate was divided into approximately 2:1 ratio, the larger portion was treated by the process of the invention and the smaller portion was used for control. The collection, treatment by this method of the invention, extending procedure, preparation of the individual insemination doses, and storage thereof was identical to the manipulations detailed in Example XI. The preparation of the control doses was identical to the normal processing procedure of the commercial cattle semen processing station at which the test was made.

The results of this test, which involved a total of 2,600 born calves, are given in Tables IX, X, XI, and XII.

Table XI

| | (Low pH Values) | | | |
|---|---|---|---|---|
| Test No. | Nominal Electrical sign of treating agent* | pH | Total No. | Sex Ratio M/F |
| 5 | Negative | 6.0 | 127 | 1.49:1 |
| 6 | Negative | 6.3 | 121 | 1.45:1 |
| 7 | Negative | 6.3 | 170 | 1.34:1 |
| 8 | Negative | 6.5 | 73 | 1.31:1 |

Table XI-continued

| | (Low pH Values) | | | |
|---|---|---|---|---|
| Test No. | Nominal Electrical sign of treating agent* | pH | Total No. | Sex Ratio M/F |
| 9 | Negative | 6.6 | 139 | 1.17:1 |

*Cation exchange resin - "Dowex-50W"

Comparison of Table IX with the following Table X shows the above-mentioned change in the acidic-alkaline relationships between the resin and the spermatozoa brought about by changing the pH of the system, and that this change is accompanied by changes in the sex-ratio of the animals conceived.

Table X

| | (Higher pH Values) | | | |
|---|---|---|---|---|
| Test No. | Nominal Electrical sign of treating agent | pH | Total No. | Sex Ratio F/M |
| 10 | Negative | 6.9 | 444 | 1.18:1 |
| 11 | Negative | 7.3 | 93 | 1.28:1 |
| 12 | Negative | 7.5 | 157 | 1.57:1 |

*Cation exchange resin - "Dowex 50W"

When a positive electrical charged treating agent was used, a change was observed in the opposite direction as seen below in Tables XI and XII:

Table XI

| Test No. | Nominal Electrical sign of treating agent | pH | Total No. | Sex Ratio F/M |
|---|---|---|---|---|
| 13 | Positive | 7.05 | 170 | 1.08:1 |
| 14 | Positive | 7.20 | 173 | 1.16:1 |
| 15 | Positive | 7.24 | 183 | 1.59:1 |
| 16 | Positive | 7.30 | 170 | 1.59:1 |
| 17 | Positive | 7.32 | 175 | 1.27:1 |

*Anion exchange resin, Dowex 1

Table XII

| Test No. | Nominal Electrical sign of treating agent | pH | Total No. | Sex Ratio F/M |
|---|---|---|---|---|
| 18 | Positive | 7.50 | 176 | 1.31:1 |
| 19 | Positive | 7.83 | 229 | 1.46:1 |

*Anion exchange resin, Dowex 1

Tables XI and XII show that the negatively charged male spermatozoa are attracted to the positively charged resin in the vicinity of pH 7.3; thus resulting in more female births as in Table VIII. Likewise, at pH 7.8 a reversal has taken place. Table XII, however, adds a reading at pH 7.5. This indicates that the reversal takes place at a rather sharply defined point on the pH scale.

The most significant features of Tables IX to XII are that they represent such a large number of cows that the results cannot be ignored on the basis of insufficient numbers to be statistically convincing. A second feature is that the results show consistency and therefore repeatability of performance. Another feature is that a useful procedure has been proven. For example, in the beef industry a ratio of higher than about 70% males is undesirable because approximately 30% females are needed to maintain a heard. My process (see Table IX Test No. 5) provides a way to produce approximately 60% males. In at least one specific embodiment, this is a major advance in the desired direction.

In addition, this was achieved under conditions in which the loss of spermatozoa was minimal (corresponding roughly to only the separated portion), and the conception rate using the treated spermatozoa was so high as to be virtually normal.

EXAMPLE XIII

Other generalized tests were run to demonstrate different embodiments of the invention. For instance, it is possible to sensitize the spermatozoa with one charged resin or other charge then to "flocculate" with another.

A sample of cattle semen was diluted to a concentration of about 30 million motile sperm per ml with a solution in water of 2-8 wt. % sodium citrate and 6.25 ppm of negatively charged poly(acrylic acid: sodium salt). The pH was 6.5. Very little flocculation was evident when observed at 100X or 430X under the microscope.

To 0.8 ml of this treated semen was added 0.1 ml of an isotonic solution of positively charged poly(ethylenimine) at a concentration of 10 ppm. When this sample was re-examined at 100X or 430X, the spermatozoa were seen to be flocculated to a very great extent. Thus, the sperm were "sensitized" (or given) increased electrostatic potential on each sperm with a charge opposite to that of the treating agent by first treating with a dilute anionic polyelectrolyte; then being "flocculated" with a cationic polyelectrolyte; inversion of the order is operable with appropriate change in pH and diluent composition as previously delineated.

EXAMPLE XIV

BaSO$_4$ was (and can be) utilized to facilitate settling of the sperm/buffer mixture, which tends to settle out faster with any heavy inert reagent (such as or equivalent to BaSO$_4$) that has been added thereto for the purpose, including other heavy minerals; bentonite clay and the like.

This variation of the method and technique of the present invention demonstrates the efficacy of increasing the density factor according to the well-known Stoke's equation for settling of suspended particles.

A suspension of powdered barium sulfate in another Krebs-Henseleit-Ringer (i.e., "K-H-R") buffer was prepared, and allowed to settle for one minute.

The supernatant suspension involved was decanted and the pH thereof adjusted to 6.8 with 0.154 Molar KH$_2$PO$_4$ solution. Bull semen was diluted to a concentration of 120 million motile sperm per milliliter (i.e. ml) using this pH regulated barium sulfate suspension in the isotonic K-H-R diluent.

To this preparation there was now added and equal volume of 1000 ppm of poly(acrylic acid): Sodium Salt (Rohm & Haas "ASR 60") in the K-H-R buffer that had also been adjusted to pH 6.3 with 0.154 Molar aq. Na$_2$HPO$_4$. Almost immediately upon mixing these two dispensions, flocculation occurred. This involved the polymer, the barium sulfate, and the spermatozoa. All of this rapidly settled to the bottom of the treating vessel. The supernatant contained essentially only solitary, freely-moving spermatozoa in a quantity equal to about one half of those originally present.

EXAMPLE XV

Further illustrating the embodiment of Example XIV, nine female cattle were inseminated in an experimental series in which three sperm samples were untreated, three sperm samples were treated with a positively-charged agent (i.e., "PEI"), and three sperm samples were treated with a negatively-charged agent (i.e., "SPA") and a weight-increasing agent (BaSO$_4$). After normal gestation periods, the calves were born and examination thereof gave the data illustrated in the following Table XIII.

Table XIII

| Cow No. | Treatment | | | | Sex |
|---|---|---|---|---|---|
| 1 | Control | | | | Male |
| 2 | Control | | | | Female |
| 3 | Control | | | | Twins, 1 Male, 1 FM[a] |
| 4 | 800 ppm PEI[b], | BaSO$_4$, | Suspension[c], | pH 6.9 | Female |
| 5 | " | " | " | " " | Female |
| 6 | " | " | " | " " | Female |
| 7 | 800 ppm SPA[d], | BaSO$_4$, | Suspension[c], | pH 7.5 | Male |
| 8 | " | " | " | " " | Male |
| 9 | " | " | " | " " | Male |

[a](FM) means free-Martin female, which is a female twin of a mixed pair which never develops secondary sexual characteristics and is incapable of ever developing into a sexually mature fledged female animal.
[b]PEI means poly(ethylene imine).
[c]BaSO$_4$ Suspension means the supernatant of powdered BaSO$_4$ in K-H-R buffer upon standing for one minute after thorough agitation.
[d]SPA means K-H-R salts of poly(acrylic acid).

EXAMPLE XVI

A copolymer of 60 weight % vinylidene chloride with 40 weight % acrylic acid was prepared by the constant vapor pressure - temperature-concentration method of Chaney.

After isolation of the copolymer, dispersions in K-H-R buffer at 1000 ppm of the copolymer were prepared and adjusted to pH 6.9 and 7.5 respectively.

Comparison of settling rates of bull sperm flocculated by this high specific gravity (viz., chlorine-containing) polyelectrolyte with those of the lower specific gravity poly (acrylic acid : sodium salt) show that the higher density flocks of spermatoza and polymer settled appreciably faster than with the lower density polyelectrolyte. The supernatant fluid contained live, solitary, motile sperm cells in all cases.

EXAMPLE XVII

In an experiment using a columnar bed of the weakly basic ion exchange resin described in Example X, Table VII, adjusted to pH 6.0 as the treating agent for rabbit spermatozoa several ejaculates were obtained from male rabbits and washed twice with 0.05 m phosphate-citrate diluent and concentrated by centrifugation. Two (2) ml of the washed rabbit spermatozoa was percolated through the column of ion exchange resin. Eight ml of the effluent was centrifuged and re-suspended in 2.5 ml of diluent for insemination.

Doe rabbits were injected with 2.5 mg of pituitary luteinizing hormone and inseminated with 0.5 ml of sermatozoan suspension, which contained approximately 24 million of live treated rabbit spermatozoa.

The female rabbits were allowed to give live birth to the offspring. Examination of the gonodal tissue of the young by sectioning, staining and microscopic examination showed a sex-ratio of these to be six females and two males or 75% females.

The significance of this experiment is that the predominant sex obtained was the same in this experiment as that of the in vitro tests with human spermatozoa determined by the numerous F-body data of Example X, and the cattle tests given in Example XV.

EXAMPLE XVIII

A sample of human spermatozoa in phosphate-citrate diluent was divided into two equal parts. One part was treated for one-half hour with an enzyme, trypsin, at a pH of 7.2. Both parts were then passed through a column charged with Dowex 50W (hydrogen form) (negative) at a pH of 6.5. The portion which received no enzyme treatment exhibited a predominance of F-bodies similar to the tests of Table VII, i.e. 1.30 / 1.00. The enzyme treated portion exhibited a ratio of F-bodies to control of only 0.91 / 1.00.

This alteration of the F-body ratio was presumably due to the enzyme action on the cell membrane of the spermatozoa and indicates the importance of environmental changes on the spermatozoa and their selective separation behavior.

EXAMPLE XIX

In another test, human spermatozoa was "stained" at a pH of 7.2 with a positively charged treating agent which was a microgel of a quaternized copolymer of vinyl benzyl chloride with 0.3 weight % of divinyl benzene. Ultra-violet fluoresence microscopy at about 970X showed that the positively charged microgel was attached to approximately half of the living spermatozoa, in a manner which appears visually to be identical to the manner in which quinacrine concentrates on the F-body in the quinacrine staining technique of male spermatozoa identification.

Since my tests have shown (and confirmation continues to come in) that the resin under these conditions is attached to the male spermatozoa, and conversely to the females when a negatively charged resin is used, I can use this method either as an in vivo or invitro means of identifying sex ratios of spermatozoa samples. Moreover, it has unique advantages in that it can be done very rapidly and with a loss of only a relatively small proportion of a living sample. Thus it can be done prior to the application of further separation techniques such that a naturally occurring imbalance in the spermatozoa of a given male on a given day can be detected immediately, and thereafter enhanced by an appropriate selection of treatment rather than by applying a treatment that is opposite to a given natural imbalance. In addition, the in vivo "staining" technique of this embodiment of my invention provides an excellent adjunct to Example XIII described above, because once the sample has been "stained" its further separation by the embodiment of Example XIII can be performed. An additional advantage over quinacrine staining is that the resins do not fade whereas quinacrine does.

Accordingly it is my intention to claim this staining technique per se, and separately from the remaining embodiments.

EXAMPLE XX

I have mentioned that electrophoresis may be employed to accelerate separation once the charge-bearing material of my invention has become attached to the spermatozoa (or vice-versa). This can be readily seen by using an electrophoresis cell suitable for microscopic observation at 100X or more.

Identical cells containing about 30 million cattle spermatozoa in K-H-R diluent were prepared; one contained, in addition, 12.5 ppm of the K-H-R salts of poly(acrylic acid) (negative) as a charge-bearing material in accordance with my invention.

When a potential of about 5 volts was applied to the cells, part of the spermatozoa of the treated sample were seen to migrate to the anode, even though they were motile and continued to struggle to escape. No accumulation of spermatozoa was observed at the cathode.

In the blank sample at 7–8 volts, no appreciable amount of spermatozoa migration was noted. When the voltage was increased to values over 8 volts, some migration was observed initially, but also electrolysis of the diluent set in forming gas bubbles at the electrodes, which in turn very soon interfered with the electrophoresis to the extent that further migration ceased.

Another experiment exhibited similar results when spermatozoa were treated with 12.5 ppm of poly(ethyleneimine), excepting, of course, that the major migration at 5 volts was toward the cathode. These tests illustrated the feasibility of accelerating the separation of spermatozoa by the combination of first attaching the spermatozoa to a polyelectrolyte and then enhancing separation by electrophoresis. Moreoover, two oppositely charged materials (of the appropriate size and selected in relation to their molecular to their molecular architecture in remain separated in isotonic solutions) may be used simultaneously and attached to oppositely charged spermatozoa of the same sample, whereupon they may be simultaneously separated selectively by electrophoresis under conditions in which sedimentation or gravity, or size, weight, and motility differences would be ineffectual. Accordingly this embodiment has distinct and unique advantages and I intend to claim it per se, and apart from the other embodiments.

EXAMPLE XXI

In another embodiment the charge-bearing treating agent is taken orally or injected into the animal. In this case the molecules must be small enough to pass through body membranes, but yet, in the presence of spermatozoa, they must be able to aggregate to the size required for the aglutination of spermatozoa. A material capable of doing this is "Tris-Maleate" (the salt of Tris (hydroxymethyl) amino methane (a poly-hydroxy compound) with maleic acidI).

In a test employing this material at various molarities, I obtained the following interesting results which indicate feasibility of controlling sex ratio by its use.

Table XIV

| Molarity of Tris-Maleate | pH | F-Bodies, % of Control Clustered | Unclustered |
|---|---|---|---|
| 0.02 | 6.0 | 1.19 | 1.45 |
| 0.03 | 6.0 | 0.78 | 2.01 |
| 0.05 | 6.0 | 0.72 | 1.01 |

EXAMPLE XXII

Separation can also be accelerated or controlled magnetically. For example, a suspension of barium ferrite powder sold by the Stockpole Carbon Company at St. Mary's Pa., was prepared in K-H-R buffer adjusted to pH 6.9. It was then allowed to stand after mixing for one minute. Then, the supernatant was decanted. This decanted suspension of finely divided barium ferrite was then used to dilute raw rabbit semen in the ratio of one volume of semen to four volumes of the barium ferrite dispersion. To five volumes of this mixture, there was added five volumes of a solution of 1000 ppm poly(acrylic acid: sodium salt) in K-H-R buffer, which had been adjusted to pH 5.9. A sample of the mixture of live sperm cells, polyelectrolyte, and magnetically susceptible particle in isotonic diluent was the placed in the well of a culture-type microscope slide and observed at 100X magnification, both under the influence of and without the influence of the magnetic field of a bar magnet. Some settling of a portion of the live sperm by gravity took place due to the density of barium ferrite. However, the movement of the barium ferrite-sperm cell-polyelectrolyte segregated sperm cells could be directionally controlled by the magnet and their settling rate could be increased or decreased by the pull of the magnet; whereas the unaffected "free" spermatozoa were not similarly affected. This technique can be also used to separate spermatozoa into two fluid streams, one predominantly male-determining and the other predominantly female-determining.

I claim:

1. In a process for altering the sex ratio of mammals in which process live spermatozoa are treated in order to separate them into two groups each of which comprises a predominance of spermatozoa having only one sex bearing characteristic, the steps of:
preparing a substantially isotonic solution for diluting and maintaining the life of spermatozoa of a given species,
obtaining a sample of live spermatozoa of that species which sample has a substantially normal male-to-female ratio,
admixing the sample and the solution and subjecting the sample in said solution to an effective amount of polyelectrostatic charge-bearing material which is, in itself, a nonconductor of electrocity and which provides a multiplicity of electrostatically charged sites predominantly of one electrostatic sign,
controlling the solution, with respect to its pH and the ionic environment it provides for the spermatozoa and the materials, substantially to maintain the spermatozoa in an electrostatically charged state in which the spermatozoa of one sex have an effective electrostatic charge opposite to that of the other sex in substantially the same ratio as is found in nature, and to maintain the poly-electrostatic charge-bearing material in a state in which together with ions in the solution it provides a predominance of charged sites of only one electrostatic sign, whereby spermatozoa of one of said groups become attached to said poly-electrostatic charge-bearing material,
thereby separating the spermatozoa into a fraction in which the spermatozoa are handicapped in their ability to move freely and into another fraction in which the spermatozoa are freely mobile and more capable to move to the ova, thus enhancing the probability of fertilizing ova with spermatozoa of only one of said groups.

2. A process in accordance with the process of claim 1 wherein the charge-bearing material is selected from the group consisting of: sulfonated styrene polymers and alkali metal salt forms thereof; acrylic and methacrylic acid polymers; itaconic acid polymers; acrylate and methacrylate polymers and alkali metal salt forms thereof; vinyl pyridines; vinyl pyrroles; polymers of N-vinyl pyrrolidones; polymers of N-vinyl oxazolidinones; sulfonic acid polymers; gels of carboxymethyl cellulose-silicic acid compounds; condensation products of phenol sulfonic acids with aldehydes; maleic anhydride polymers; nucleophilic reaction products of polymers of halo-akyl vinylidene aromatic compounds; positively-charged silver halide sols; and charged clays.

3. A process in accordance with the process of claim 1 wherein the charge-bearing material is a cross-linked polymeric material.

4. A proces in accordance with the process of claim 1 wherein the charge-bearing material is selected from the group consisting of linear, branched, ladder and cross-linked natural and synthetic organic polyelectrolytes, organic and inorganic electrostatically charged colloids and semi-colloids, electrostatically charged hydrocarbon dispersions, and natural lattices.

5. A process in accordance with the process of claim 1 wherein the charge-bearing material is selected from the group of synthetic ion-exchange materials comprising:
a strongly acidic sulfonated polystyrene cation exchange resin (in sodium ion form) copolymerized with divinylbenzene to provide cross-linking and containing bound sulfonic acid groups; or
a strongly basic anion exchange resin (in chloride ion form) having a polystyrene matrix copolymerized with divinylbenzene to provide cross-linking, and containing bound trimethyl benzyl ammonium groups.

6. A process according to claim 1, wherein an additional separation force, selected from the group consisting of: mechanical action by attachment of the charge-bearing material to a fixed base, mechanical action brought about by the inertia of the charge-bearing agent per se, gravity, centrifugal force, electrophoretic-induced force, and magnetic force, is applied so as to act upon the charge-bearing material which is attached to a portion of the spermatozoa.

7. A process according to claim 1 wherein two charge-bearing materials having charges of opposite sign are employed.

8. A process according to claim 1 wherein the charge-bearing material is an ion-exchange resin.

9. A process according to claim 1 wherein the charge-bearing material has a positive charge and the pH is adjusted to about 7.2 whereby attachment to the male bearing spermatozoa is effected.

10. A process according to claim 1 wherein the charge-bearing material has a negative charge and the pH is adjusted to about 6.0 whereby attachment to the female spermatozoa is effected.

11. A process according to claim 1 wherein the group to which the material is attached is employed for fertilization.

12. A process according to claim 1 wherein the group to which the material is not attached is employed for fertilization.

13. A process according to claim 1 wherein the effective electrostatic charge of the spermatozoa of one sex-determining character is altered and the preferential handicapping thereof is accomplished comprising the steps of (a) the addition to said spermatozoa of at least one poly-electrostatic material having a plurality of charge sites whose electrostatic charge is the opposite to that of the spermatozoa which are to be preferentially handicapped, thereby effecting a de facto reversal of the effective electrostatic charge of these spermatozoa, followed by (b) admixture with a spermatozoa-separating poly-electrostatic charge-bearing material which has a predominantly opposite electrostatic charge as compared to that of the poly-electrostatic material of step (a), thus causing the handicapping of one portion of the spermatozoa in regard to their ability to move and to fertilize ova.

14. The process according to claim 1 comprising, after the step of separating the spermatozoa, the additional step of liberating the handicapped spermatozoa from the effect of the poly-electrostatic charge-bearing material.

15. The process of claim 1, wherein the poly-electrostatic charge-bearing material comprises a carboxylated polymer.

16. A process for identifying the sex bearing characteristic of spermatozoa comprising the steps of:

preparing a substantially isotonic solution for diluting and maintaining the life of spermatozoa of a given ratio, obtaining a sample of live spermatozoa of that species which sample has a substantially normal male-to-female ratio, admixing the sample and the solution and subjecting the sample in said solution to a poly-electrostatic charge-bearing material which is, in itself, a nonconductor of electricity and which provides a multiplicity of electrostatically charged sites predominantly of one electrostatic sign, controlling the solution, with respect to its pH and the ionic environment it provides for the spermatozoa and the material, substantially to maintain the spermatozoa in an electrostatically charged state in which the spermatozoa of one sex have a charge opposite to that of the other sex in substantially the same ratio as is found in nature, and to maintain the charge-bearing material in a state in which together with ions in the solution it provides a predominance of charged sites of only one electrostatic sign, whereby spermatozoa of one of said groups become attached to said charge-bearing material, subjecting a sample of the solution containing the spermatozoa to an electric field to which the charge-bearing material responds to a greater degree than do the spermatozoa and the surrounding medium.

17. A process according to claim 16 wherein two charge-bearing materials having charges of opposite sign are employed.

18. A process according to claim 7 wherein the two materials are employed in sequence.

19. A process according to claim 7 wherein the two materials are employed simultaneously.

20. A process for identifying the sex bearing characteristic of spermatozoa comprising the steps of:

preparing a substantially isotonic solution for diluting and maintaining the life of spermatozoa of a given ratio, obtaining a sample of live spermatozoa of that species which sample has a substantially normal male-to-female ratio, admixing the sample and the solution and subjecting the sample in said solution to a poly-electrostatic charge-bearing material which is, in itself, a nonconductor of electricity and which provides a multiplicity of electrostatically charged sites predominantly of one electrostatic sign, controlling the solution, with respect to its pH and the ionic environment it provides for the spermatozoa and the material, substantially to maintain the spermatozoa in an electrostatically charged state in which the spermatozoa of one sex have a charge opposite to that of the other sex in substantially the same ratio as is found in nature, and to maintain the charge-bearing material in a state in which together with ions in the solution it provides a predominance of charged sites of only one electrostatic sign, whereby spermatozoa of one of said groups become attached to said charge-bearing material, and identifying the spermatozoa to which the polyelectrostatic charge bearing material is attached by applying to said solution an electromagnetic radiation of a wave length which stimulates from said poly-electrostatic charge bearing material an observable response differing from the response thereto of the spermatozoa to which the material is not attached.

* * * * *